United States Patent [19]
Trebosc et al.

[11] Patent Number: 6,054,138
[45] Date of Patent: Apr. 25, 2000

[54] STABILIZED PSEUDO-EMULSIONS AND THEIR PREPARATION PROCESS

[75] Inventors: Marie-Thérèse Trebosc, Castres; Jacques Dubois, Narbonne, both of France

[73] Assignee: Pierre Fabre Dermo-Cosmetique, Boulogne, France

[21] Appl. No.: 08/952,647

[22] PCT Filed: May 21, 1996

[86] PCT No.: PCT/FR96/00756

§ 371 Date: Nov. 21, 1997

§ 102(e) Date: Nov. 21, 1997

[87] PCT Pub. No.: WO96/37180

PCT Pub. Date: Nov. 28, 1996

[30] Foreign Application Priority Data

May 22, 1995 [FR] France .................. 95 06044

[51] Int. Cl.[7] .................. A61K 7/00; A61K 7/42; A61K 31/74; A61K 47/00
[52] U.S. Cl. .................. 424/401; 424/59; 424/78.03; 514/777; 514/781; 514/786; 514/787; 514/844; 514/937
[58] Field of Search .................. 424/401, 59, 78.03; 514/781, 777, 786, 787, 844, 937

[56] References Cited

U.S. PATENT DOCUMENTS

| | | | |
|---|---|---|---|
| 4,963,656 | 10/1990 | Mitani | 530/353 |
| 5,075,113 | 12/1991 | DuBois | 424/450 |
| 5,478,555 | 12/1995 | Bara et al. | 424/78.03 |
| 5,637,291 | 6/1997 | Bara et al. | 424/59 |
| 5,725,844 | 3/1998 | Gers-Barlag et al. | 424/59 |
| 5,804,167 | 9/1998 | Schonrock et al. | 424/59 |
| 5,833,951 | 11/1998 | Atrz et al. | 424/47 |
| 5,874,092 | 2/1999 | Roulier et al. | 424/401 |

FOREIGN PATENT DOCUMENTS

| | | |
|---|---|---|
| 0293766 | 5/1988 | European Pat. Off. |
| 0328355 | 2/1989 | European Pat. Off. |
| 2710263 | 9/1993 | France . |
| 4425268 | 7/1994 | Germany . |
| 61-133138 | 6/1986 | Japan . |
| 96/02223 | 7/1994 | WIPO . |
| 9602223 | 2/1996 | WIPO . |

OTHER PUBLICATIONS

The Merck Index, p. 5452 and 5453 at 5452 Lecithin, 1996.

*Primary Examiner*—Shelley A. Dodson
*Assistant Examiner*—Marina Lamm
*Attorney, Agent, or Firm*—The Firm of Gordon W. Hueschen

[57] ABSTRACT

The present invention relates to a pharmaceutical and/or cosmetic composition in the form of a stabilized pseudoemulsion, characterized in that it is essentially comprised of (1) at least one aqueous phase containing a single gelifying agent selected from the group comprising polyoses, such as gelose, the xanthane gums, cellulose, alginates, semisynthetic derivatives of cellulose, and acrylic polymers such as Synthalen®; (2) at least one lipidic phase containing at least one consistency factor, with a ratio consistency factor/total lipidic phase between about 0.06 and 0.18, and in that said composition is free of surfactants. It also relates to a process for preparing such composition.

22 Claims, 1 Drawing Sheet

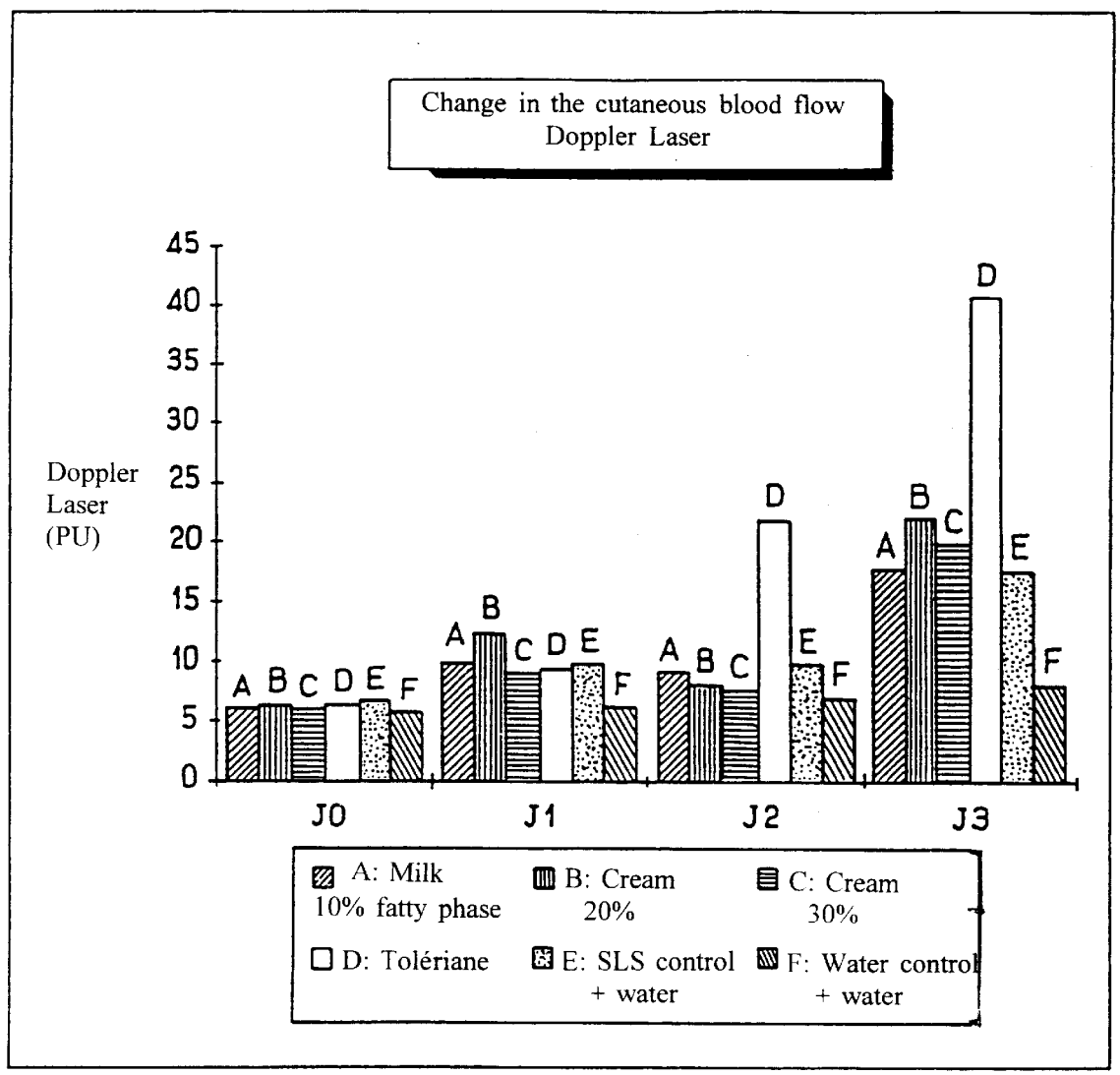
FIG_1

STABILIZED PSEUDO-EMULSIONS AND THEIR PREPARATION PROCESS

The present application is a U.S. National Application filed under 35 USC 371 of PCT/FR96/00756, filed May 21, 1996 based upon French application Ser. No. 95/06044 filed May 22, 1995.

The present invention relates to new formulations of heterogeneous galenic compositions which can be employed especially in dermatology and in cosmetology.

Heterogeneous galenic forms constitute the ultimate degree of complexity, because of the presence of compounds which are both lipophilic and hydrophilic: their purpose is to clean, treat, protect and beautify the skin with concern for the care, comfort and pleasure of the user.

The art of galenics has always found its letters patent of nobility in the production of emulsions.

This art has essentially always consisted of the research and/or the development of emulsifying or surface-active substances which can produce a stable suspension of oil and water, which are renowned for being immiscible.

These emulsifiers are always of various origins: synthetic for the most part or natural, such as, for example, lecithins.

Regardless of their origins and of the strength of their emulsifying power, the part played by an emulsifier can be likened to that of the detergents which are known for their reactivity both on textile fibers and on cutaneous tissues.

For reasons of industrial manufacture and of physical stabilities in time, all cosmetic emulsions contain emulsifiers the nature of which may be nonionic (e.g. optionally oxyethylenated derivatives of sorbitol, sucrose derivatives), anionic (fatty acid salts) or cationic (quaternary ammonium derivatives) nevertheless the least frequently employed because they are classed among the most reactive and more recently emulsifying polymers known by the name of Pemulen®.

However, even when chosen among the best ones, these emulsifiers remain dangerous to the skin for a number of reasons.

The skin is covered with a protective film, called hydrolipid surface film (HLSF) and consisting predominantly of fatty substances excreted by the sebaceous glands and of lipids originating from the degradation of the cells during the keratinization phase of the corneous cells.

When spread onto the skin, the emulsion is dissociated and the outer aqueous phase evaporates off leaving in place the emulsifier which exhibits an affinity for the oils or fatty substances of the (HLSF); it thus facilitates the subsequent removal of this film from the surface of the epidermis.

This film will thus be impoverished day after day. Only fatty skins, extensively provided with sebumsecreting sebaceous glands will be able to compensate for this destruction. However, the phenomenon of reactional seborrhoea is nevertheless known, caused by the use of surfactants which are too reactive for daily cleaning.

As for dry skins, these are already disadvantaged by a deficient HLSF.

In addition, the lipid cement binding the corneous cells is disorganized and no longer plays its part as a barrier and on some categories of weakened skins known as sensitive, elderly people, atopic young children, some reactions will be able to occur more easily.

It is known, furthermore, that the impoverishment of this barrier effect increases the frequency of so-called orthoergic irritant reactions and that the repeated application of products on skin of this type can in the long term result in reactions of sensitization to one of the constituents—so-called allergic reactions.

In addition, emulsifiers act as adjuvants of transcutaneous entry; as such, they reveal the irritant or allergy-inducing effect of various other substances present in the formulation, which would be completely tolerated in their absence.

They have a cytotoxic effect in vitro in cell culture. This toxicity illustrates the direct action which some emulsifiers can exert according to their—nature and their concentration—on epidermic cells devoid of their weakened natural protection and then finally smoothed down because of the gradual damage suffered by the cytoplasmic membrane.

All the present emulsions contain emulsifiers in application of a fundamental principle of formulation which is definitively accepted; the formulator's role therefore consists in choosing an emulsifier and in determining its concentration. It is in this context that the Applicants have made a finding which is surprising and contrary to this fundamental principle: in some conditions it is possible to obtain heterogeneous compositions which can be likened to "pseudoemulsions", in the absence of emulsifiers.

This is why the present invention has as its subject matter a pharmaceutical and/or cosmetic composition in the form of pseudoemulsion, characterized in that it consists essentially of (1) at least one aqueous phase containing a single gelling agent,
(2) at least one lipid phase containing at least one consistency factor, with a consistency factor/total lipid phase ratio of between approximately 0.06 and 0.18 and in that the said composition is devoid of surfactants.

The compositions according to the invention are particularly suited for a topical use and play a part in protection or cleaning with a great comfort to the user, while eliminating the emulsifiers and the substances liable to be or to become allergy-inducing or irritant.

Such products will therefore have a high tolerance.

In fact, the Applicants have unexpectedly found that the elimination of emulsifiers is possible while preserving emulsions which are stable in time, by thickening the antagonist (hydrophilic and lipophilic) phases present. The two phases are thus kept intimately linked for long periods, which are compatible with the life of a cosmetic, this being so in the case of various proportions of phases, which makes it possible to envisage a whole high-tolerance range from fluid milks to very rich and compact creams.

Heterogeneous compositions are obtained the microscopic structure of which differs from that of an emulsion.

The consistency factor present in the lipid phase is a substance which is semisolid at ambient temperature and with a melting point higher than 50° C.; when dissolved in a fatty phase with heating, it recovers its semisolid consistency and, when cold, imparts to the lipid phase a viscosity and a consistency which are determined by the percentage of this substance. The consistency factor/total fatty phase ratio defines the stability of the product over time.

According to a particularly preferred aspect of the invention this ratio is between 0.08 and 0.15.

The compositions according to the invention exhibit a good stability after 5 months at 40° C., both in the case of the fluid forms and in the case of the creams.

These consistency factors are chosen from waxy fatty substances such as hydrocarbons saturated, triglycerides and vegetable fats which have a melting point higher than 50° C., mono- and diglycerides. These substances may be of animal, vegetable or synthetic origin. The choice made is the synthetic one, which allows a greater uniformity in the physicochemical characteristics, especially in the case of the mono- or diesters of glycerols, in the case of which the relative percentage of the mono- or diglycerides will be capable of varying from 40 to 100%. The glycerol esters employed as consistency factor have no surfaceactive action: they have an HLB close to 3 and are essentially lipophilic.

A wide choice of composition of the fatty phase is made possible by the preferential solubilities of each of the glycerol esters in a very wide range of fatty oils or esters: for example, vegetable oils, mineral oils, perhydrosqualene, isopropyl palmitate, silicone oils producing oily phases which are more or less rich, more or less fluid, with varied spreading, entry and residual effect.

The aqueous phase can be thickened by gelling agents which are known to a person skilled in the art.

These substances are intended to impart consistency to the preparation by increasing the viscosity of the aqueous phase. For this use polymers are employed, which have the property of forming a macromolecular network in the presence of water: a gel.

The polymers may be of vegetable origin: polyoses (polysaccharides): agar, gum, in particular xanthan gums, cellulose, alginates or semisynthetic derivatives, in particular cellulose derivatives like methyl cellulose, ethyl cellulose, hydroxypropyl methyl cellulose, which are products widely employed because of their flexibility in use.

They can also be of mineral nature: silicas, silicates, bentones, or else synthetic, like acrylic polymers: carbopols (or carbomers), which are acidic substances which must be neutralized at the time of use to form the polymer: this product is therefore always accompanied by an alkali (in general an organic base such as triethanolamine).

Among synthetic acrylic polymers, the Synthalen® grade, (homopolymer of acrylic acid marketed by the company 3V-Sigma), devoid of synthesis residues such as benzene, is particularly suitable.

The compositions according to the invention will be preferably devoid of perfume.

They may additionally contain a compound which is active by topical route, soluble in one and/or other of the emulsion phases, which will serve as a carrier for the active principle. Among the active principles liable to form part of the compositions according to the invention there may be mentioned those possessing properties of a hydrating agent, emollient, kerato-plastic, regenerator, and the like.

The pseudoemulsions according to the invention are particularly suited for the preparation of sun creams, by incorporation of a filter or of a sunscreen.

According to a particularly advantageous embodiment preserving agents are also absent from the compositions according to the invention.

They are suited for an application to healthy skin and also, because of their complete tolerance, to injured skin (superficial abrasion, burns) and to the mucosa. The absence of preserving agents constituting an additional winning argument for such uses.

This perfect tolerance has been demonstrated by an epicutaneous test under occlusive patch of 24 hours on healthy skin and on skin which is injured (by lauryl ether sulfate at 0.5% strength).

The evaluation of cutaneous tolerance is followed by the measurement of microcirculation with the doppler laser.

It is known that preserving agents (although authorized) finish by causing allergic reactions due to their repeated use.

In this case the most reputed ones are those which release formalin, the substance called Kathon CG (isothiazolone derivatives) and even parabens (parahydroxybenzoic esters).

Their pure and simple elimination enables many users, already sensitized both by cosmetic and medical specialties (many topicals containing parabens), to be able to employ these products without fear.

In addition, no other substance which has bacteriostatic properties but which is not listed in the positive list of the EEC is introduced here, in order to avoid causing such disadvantages in the long term.

The same concern has resulted in the elimination of perfumes or any substance introduced to perfuming compositions liable to mask odors.

In return, this elimination imposes a special severity in the choice of the raw materials employed in the formulations: their nature, their quality and their chemical purity must be like their odorant character, clean very weak or nil.

The production of this type of mixture on the industrial scale requires very special manufacturing processes which are complicated by the fact of the absence of preserving agents.

This is why the present invention also has as its subject matter a process for the preparation of a composition in the form of emulsion devoid of surface-active agents, characterized in that the following steps are performed, in sterile atmosphere:

a) preparation of the aqueous and lipid phases respectively, at a temperature higher than or equal to approximately 70° C., b) introduction, with high stirring, of the lipid phase into the aqueous phase, while maintaining the temperature higher than or equal to approximately 70° C., c) cooling the mixture to a temperature higher than or equal to approximately 25° C., with moderate stirring, d) recovery of a sterile smooth emulsion.

The definitive appearance of the product is reached only at the temperature of 25° C., where both phases end by being perfectly smoothed.

In this process any solid substance must be sterilized beforehand and introduced either directly using vacuum into the reactor (according to the fluidized bed technique), or dissolved beforehand in a solution which will have to undergo a preliminary sterilizing filtration.

Each of the phases is maintained at a temperature higher than 70° throughout the period of the mixing, of the filtration and of the transfer into the manufacturing vessel, by lagging systems.

The process of manufacture is original in the sense that the fatty phase maintained at 70° is introduced with high stirring of Turbine type during a very short time—5 to 10 min into the aqueous phase which is slightly gelled by a partial neutralization; the stirring speed will be advantageously between 20 and 30 m/s. The end of the neutralization is next performed before cooling under moderate stirring; the latter may be obtained more particularly using Helix, anchor systems at speeds lower than or equal to approximately 2 m/s.

Next, the storage and the distribution into packages which are sterile themselves ensure perfect protection.

The examples which follow are intended to illustrate the invention without limiting its scope in any way.

In these examples reference will be made to the appended FIGURE, which shows the change in the cutaneous blood flow after application of compositions under occlusive patch.

EXAMPLE 1

Milk for Removing Make-Up

| Aqueous phase: 90% | |
| --- | --- |
| - demineralized or thermal water | 79 to 75 g |
| - glycerine | 11 to 15 g |
| - carboxyvinyl polymer: (without trace of benzene) | 0.3% |
| - extra pure triethanolamine | q.s. pH 6 |
| Fatty phase: 10% | |
| - liquid paraffin | 8.5 g |
| - glycerol monostearate: | 1.5 g |

EXAMPLE 2

Cream for Dry and Sensitive Skins

| Aqueous phase: 80% | |
| --- | --- |
| - demineralized water | 69 to 65 g |
| - glycerine | 11 to 15 g |
| - carboxyvinyl polymer: (without benzene) | 0.25% |
| - extra pure TEA | q.s. pH 6 |
| Fatty phase: 20% | |
| - glycerol monostearate (40%) | 2.4 g |
| - mineral oil | 5 g |
| - silicone oil | 2 g |
| - vegetable oil | 6.6 g |
| - perhydrosqualene | 5 g |

To this phase may be added natural vitamin E or the acetate form at maximum 0.5% strength as protection against oxidation.

| Other example of the fatty phase: 20% | |
| --- | --- |
| - glycerol monostearate containing 100% of monoester | 2.5 g |
| - cyclomethicone | 6 g |
| - cosbiol | 7.5 g |
| - sesame oil | 4 g |

EXAMPLE 3

Cream for Delipidized or Atopic Skins

| Aqueous phase: 70% | |
| --- | --- |
| - demineralized or thermal water | 59 to 55 g |
| - glycerol | 11 to 15 g |
| - carboxyvinyl polymer: | 0.2% |
| Fatty phase: 30% | |
| - glycerol monostearate: | 2.6 g |
| - vegetable oil: | 15.4 g |
| - perhydrosqualene: | 8 g |
| - fluid paraffin: | 4 g |

EXAMPLE 4

Total Sunscreen Cream

In the preceding Example 4 to 8% of Titanium dioxide which is micronized and sterilized beforehand may be dispersed in the fatty phase.

EXAMPLE 5

Evaluation of the Cutaneous Tolerance

The study is carried out by doppler laser measurement of the cutaneous microcirculation after attack with sodium lauryl sulfate (SLS) and then application of the products under occlusive patches for 24 h.

The measurements are performed:
on D0: before any application of the product
on D1: 1 h after removal of the SLS patch
on D2: 1 h after removal of the product patches and of the water control patch
on D3: 24 h after removal of the product patches and of the water control patch
The results are shown in the appended FIGURE.

BRIEF DESCRIPTION OF THE DRAWINGS

FIG. 1 shows results of a study carried out by doppler laser measurement of the culaneous microcirculation after attack with sodium lauryl sulfate (SLS) and then application of the products under occlusive patches for 24 hours, the products A, D, and C corresponding to the products of Examples 1, 2, and 3, and the meanings of the symbols DO, DI, D2, and D3 being as just described in the foregoing.

This study comprises a market refernce: Toleriane presented as a product of high tolerance, without preserving agent.

The tests performed with the products A, B and C corresponding to Examples 1, 2 and 3 respectively are tolerated much better than the reference product.

The increase in the microcirculation, reflecting a local inflammation related to an irritation, is of the same order as that observed with the SLS control +water.

This increase is significantly lower than the change observed with the reference product.

We claim:

1. A pharmaceutical and/or cosmetic composition in the form of a stabilized pseudoemulsion consisting essentially of
   (1) at least one aqueous phase containing a single gelling agent selected from the group consisting of agar, xanthan gums, cellulose, alginates, semisynthetic derivatives of cellulose, and acrylic polymers,
   (2) at least one lipid phase containing at least one consistency factor, with a consistency factor/total lipid phase ratio of between approximately 0.06 and 0.18, the said composition being devoid of surfactants,
   wherein the consistency factor present in the lipid phase is selected from the group consisting of waxes, saturated hydrocarbons, monoglycerides, diglycerides, triglycerides, and vegetable fats which have a melting point higher than approximately 50° C.

2. A composition according to claim 1, wherein the consistency factor/total lipid phase ratio is between 0.08 and 0.15.

3. A composition according to claim 1, containing at least one active principle, in at least one of the phases of the stabilized pseudoemulsion.

4. A process for the preparation of a composition in the form of a stabilized pseudoemulsion of claim 1, consisting essentially of
(1) at least one aqueous phase containing a single gelling agent selected from the group consisting of agar, xanthan gums, cellulose, alginates, semisynthetic derivatives of cellulose, and acrylic polymers,
(2) at least one lipid phase containing at least one consistency factor, with a consistency factor/total lipid phase ratio of between approximately 0.06 and 0.18, the said composition being devoid of surfactants, wherein the following steps are performed, in a sterile atmosphere:
   a) preparing the aqueous and lipid phases respectively, at a temperature higher than or equal to approximately 70° C.,
   b) introducing, with high stirring, the lipid phase into the aqueous phase, while maintaining the temperature higher than or equal to approximately 70° C.,
   c) cooling the mixture to a temperature of approximately 25° C., with moderate stirring,
   d) recovering a sterile smooth emulsion.

5. A composition obtained by the process according to claim 4, which is devoid of surfactants and of preserving agents.

6. A composition according to claim 1, having the following formulation:

| Aqueous phase: 90% | |
|---|---|
| demineralized or thermal water | 79 to 75 g |
| glycerine | 11 to 15 g |
| carboxyvinyl polymer: | 0.3% |
| (without trace of benzene) | |
| extra pure triethanolamine | q.s. pH 6 |
| Fatty phase: 10% | |
| liquid paraffin | 8.5 g |
| glycerol monostearate: | 1.5 g. |

7. A composition according to claim 1, having the following formulation:

| Aqueous phase: 80% | |
|---|---|
| demineralized water | 69 to 65 g |
| glycerine | 11 to 15 g |
| carboxyvinyl polymer: | 0.25% |
| (without benzene) | |
| extra pure triethanolamine | q.s. pH 6 |
| Fatty phase: 20% | |
| glycerol monostearate (40%) | 2.4 g |
| mineral oil | 5 g |
| silicone oil | 2 g |
| vegetable oil | 6.6 g |
| perhydrosqualene | 5 g. |

8. A composition according to claim 1, having the following formulation:

| Aqueous phase: 70% | |
|---|---|
| demineralized or thermal water | 59 to 55 g |
| glycerol | 11 to 15 g |
| carboxyvinyl polymer: | 0.2% |
| Fatty phase: 30% | |
| glycerol monostearate: | 2.6 g |
| vegetable oil: | 15.4 g |
| perhydrosqualene: | 8 g |
| fluid paraffin: | 4 g. |

9. A composition according to claim 8, containing 4 to 8% by weight of titanium dioxide.

10. A composition according to claim 4, containing an active ingredient which is active by the topical route.

11. A composition according to claim 6, containing an active ingredient which is active by the topical route.

12. A composition according to claim 7, containing an active ingredient which is active by the topical route.

13. A composition according to claim 8, containing an active ingredient which is active by the topical route.

14. A pharmaceutical and/or cosmetic composition of claim 1 in the form of a stabilized pseudoemulsion consisting essentially of
(1) at least one aqueous phase containing a polyose as single gelling agent,
(2) at least one lipid phase containing at least one consistency factor, with a consistency factor/total lipid phase ratio of between approximately 0.06 and 0.18, the said composition being devoid of surfactants.

15. A composition of claim 1 wherein the acrylic polymer is a homopolymer of acrylic acid devoid of benzene residues.

16. A composition according to claim 2, containing at least one active principle, in at least one of the phases of the stabilized pseudoemulsion.

17. A process according to claim 4, wherein the consistency factor/total lipid phase ratio is between 0.08 and 0.15.

18. A process according to claim 4, wherein the consistency factor present in the lipid phase is selected from the group consisting of waxes, saturated hydrocarbons, monoglycerides, diglycerides, triglycerides, and vegetable fats which have a melting point higher than approximately 50° C.

19. A process according to claim 4, wherein the consistency factor/total lipid phase ratio is between 0.08 and 0.15 and wherein the consistency factor present in the lipid phase is selected from the group consisting of waxes, saturated hydrocarbons, monoglycerides, diglycerides, triglycerides, and vegetable fats which have a melting point higher than approximately 50° C.

20. A process according to claim 4, wherein at least one active principle is contained in at least one of the phases of the stabilized pseudoemulsion.

21. A process according to claim 5, wherein at least one active principle is contained in at least one of the phases of the stabilized pseudoemulsion and wherein the consistency factor present in the lipid phase is selected from the group consisting of waxes, saturated hydrocarbons, monoglycerides, diglycerides, triglycerides, and vegetable fats which have a melting point higher than approximately 50° C.

22. A process according to claim 21, wherein the consistency factor/total lipid phase ratio is between 0.08 and 0.15.

* * * * *

UNITED STATES PATENT AND TRADEMARK OFFICE
CERTIFICATE OF CORRECTION

PATENT NO. : 6,054,138
DATED : Apr. 25, 2000
INVENTOR(S) : Marie-Therese Trebose and Jacques Dubois It is certified that error appears in the above-indentified patent and that said Letters Patent is hereby corrected as shown below:

Column 6, line 30: "A, D, and" should read:
-- A, B, and --.

Column 6, line 33: "refernce:" should read:
-- reference: --.

Signed and Sealed this

Tenth Day of April, 2001

Attest:

NICHOLAS P. GODICI

*Attesting Officer*          *Acting Director of the United States Patent and Trademark Office*